United States Patent [19]

Kim

[11] Patent Number: 5,352,696
[45] Date of Patent: Oct. 4, 1994

[54] QUATERNARY NITROGEN-CONTAINING VITAMIN E DERIVATIVES AND USES THEREOF

[75] Inventor: Young D. Kim, Seoul, Rep. of Korea

[73] Assignee: Pacific Corporation, Seoul, Rep. of Korea

[21] Appl. No.: 8,564

[22] Filed: Jan. 22, 1993

[51] Int. Cl.$^5$ .................. A61K 31/355; C07D 311/72
[52] U.S. Cl. .................. 514/458; 514/844; 514/847; 549/408; 427/70; 252/308
[58] Field of Search .............. 549/408; 252/308; 514/844, 458, 847; 424/70

[56] References Cited

U.S. PATENT DOCUMENTS 2,995,513   8/1961   Paschall et al. ................ 210/54
3,532,751  10/1970   Langher et al. ............. 260/567.6
4,632,984  12/1986   Matsunaga et al. ............. 536/50
4,663,159   5/1987   Brode, II et al. .............. 424/70

*Primary Examiner*—Nicky Chan
*Attorney, Agent, or Firm*—Foley & Lardner

[57] ABSTRACT

A quaternary nitrogen-containing vitamin E and quaternary nitrogen-containing polyethoxylated vitamin E are disclosed. Methods for preparing the quaternary nitrogen-containing vitamin E derivatives which comprises reacting vitamin E or polyethoxylated vitamin E with a quaternizing agent selected from quaternary halohydrins and epoxides to effect a quaternization are also disclosed. The quaternary nitrogen-containing vitamin E derivatives show an improved substantivity to skin or hair and a good water dispersibility as well as may be employed as an useful surface active agent in cosmetics.

9 Claims, 2 Drawing Sheets

FIGURE 2

| Sample \ Average score | 0 | 0.5 | 1 |
|---|---|---|---|
| Glycerin (5%) | ▯ | | |
| Quaternary nitrogen-containing vitamin E (Example) (10%) | ▯ | | |
| Quaternary nitrogen-containing polyoxyethylene (15) tocopheryl ether (10%) | ▯ | | |
| Polyoxyethylene (20) sorbitan monostearate (10%) | ▭▭▭ | | |

QUATERNARY NITROGEN-CONTAINING VITAMIN E DERIVATIVES AND USES THEREOF

BACKGROUND OF THE INVENTION

1. Field of the Invention

The present invention relates to cationic vitamin E derivatives and uses thereof, and more particularly, to quaternary nitrogen-containing vitamin E or polyethoxylated vitamin E, which shows a high substantivity to hair or skin and a high dispersibility in water as well as may be advantageously employed as a surface active agent in cosmetics or medicines, and to uses thereof.

2. Description of the Prior Art

Vitamin E is the generic name of a mixture of lipid soluble phenols, tocopherols: and tocotrienols possessing general structural features an aromatic chromanol head and a 16-carbon hydrocarbon tail. The number of methyl substituents in the chromanol nucleus gives rise to $\alpha$, $\beta$, $\tau$, $\delta$ isomers, whereas the saturation of the hydrocarbon chain differentiates tocopherols with a saturated chain from tocotrienols with an unsaturated chain as forms of vitamin E.

Vitamin E is widely employed as an active anti-oxidation agent in drugs, foods and cosmetics. And, vitamin E is known to be useful in healing injuries and protecting the skin against the ultraviolet irradiation as well as be useful as an anti-inflammation agent.

Vitamin E is a viscous brown liquid which is soluble in oils and not soluble in water. It is considerably resistant against the heat, strong acids and visible light in the absence of oxygen species. It is, however, sensitive to the ultraviolet light, alkalis and oxygen species.

Many attempts have been made to improve the stability of vitamin E against oxidation by oxygen species. For example, lipophilic tocopherol derivatives and hydrophilic tocopherol derivatives were proposed.

Lipophilic tocopherol derivatives may include, for example, tocopheryl esters such as tocopheryl acetates, tocopheryl linolates and tocopheryl nicotinates. Tocopheryl acetates may be obtained by esterifying the tocopherols with acetic acid and are most widely employed in various fields due to their improved stability against oxidation. Tocopheryl linolates are an ester of tocopherol with linoleic acid and show an improved stability against oxidation and an improved substantivity to skin. They are recently advantageously employed in cosmetics. Tocopheryl nicotinates, which are disclosed in Japanese Patent Publication Sho 55-2431, may be obtained by reacting 1-alkyl-2-halopyridinium with nicotinic acid in the presence of a tertiary amine to give nicotinoyloxy pyridinium, which is then subjected to reaction with tocopherol in the presence of a tertiary amine. Japanese Patent Publication Sho 55-2431 teaches that the tocopheryl nicotinates exhibit capillary vasodilating and toxiciding abilities and an activity for lowering cholesterol level in blood stream and that the tocopheryl nicotinates are found to be an excellent slow-releasing drug.

Because solubility or dispersiblity in water of the liphophilic tocopherols is poor, several attempts have been made to improve these properties and, as a result, tocopherols with an improved hydrophilicity were proposed.

One example of such tocopherols with an improved hydrophilicity is d-α-tocopherylglycol 1000 succinate [The Condensed Chem. Dictionary, 1981, VAN NOSTRAND], which is an ester of tocopherol with ethoxylated succinic acid and represents the vitamin E having a good water dispersibility. This compound is employed as a food additive and used as a surfactant in cosmetics and drugs.

Another example of hydrophilic vitamin E is a polyethoxylated vitamin E which is developed by me and other colleagues and is disclosed in U.S. Ser. No. 07/857,652, now U.S. Pat. No. 5,235,073. The polyethoxylated vitamin E has an emulsifying, dispersing and solubilizing abilities and may be advantageously employed as a surface active agent in cosmetics and drugs.

Another hydrophilic vitamin E is a quaternary nitrogen-containing tocopheryl nicotinate which may be advantageously formulated into various drugs due to its physiological activities and good solubility in water or aqueous solvents. However, the above compound is quaternized at nicotinic acid moiety, not at tocopherol moiety.

Besides, the present inventor has a conception that catanionic physiologically active materials can efficiently exhibit their activity when applied to the skin or hair due to their good substantivity to the skin or hair and can exhibit good moisture retention effect due to their solubility in water or aqueous medium, and has made extensive studies to provide vitamin E derivatives exhibiting an improved substantivity to hair or skin, a high dispersiblity in water and an excellent surface activity while retaining the physiological activities of vitamin E species. As a result thereof, I accomplished the present invention.

SUMMARY OF THE INVENTION

Thus, an object of the present invention is to provide quaternary nitrogen-containing vitamin E derivatives represented by the following formula(I):

$$R_{VIT}-O-(CH_2CH_2O)_n-R^1 \qquad (I)$$

wherein:

$R_{VIT}-O-$ is a vitamin E radical, n is an integer from 0 to 30, inclusive, and $R^1$ is a quaternary nitrogen-containing substituent.

Other object of the present invention is to provide different cosmetic compositions containing as an active constituent the quaternary nitrogen-containing vitamin E derivatives (I).

BRIEF DESCRIPTION OF THE DRAWINGS

FIG. 2 is a bar graph representing the results of an eye irritation test for compounds according to the present invention as compared to comparative compounds.

DETAILED DESCRIPTION OF THE INVENTION

Figure 1:
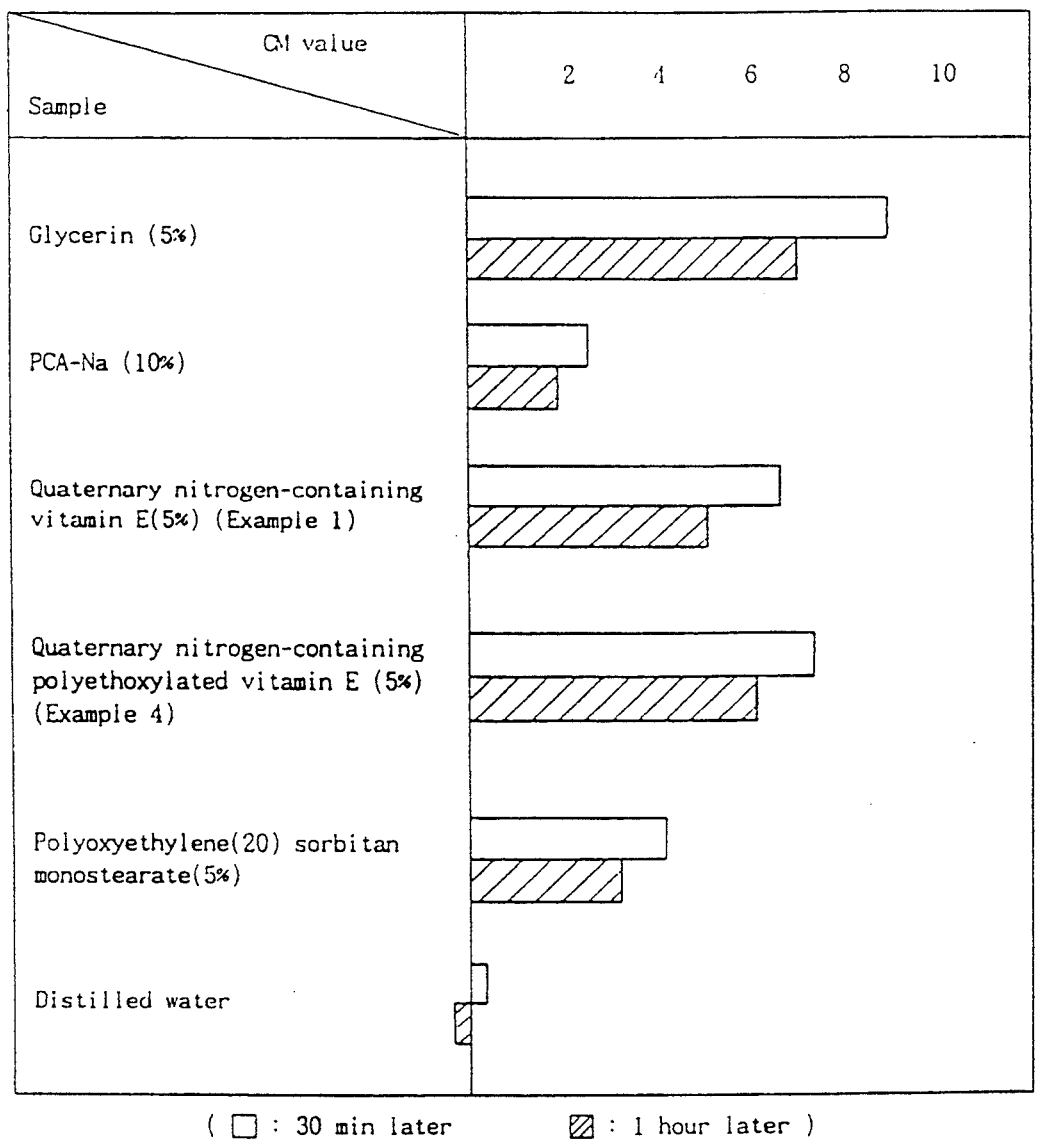
FIG. 1 is a bar graph representing the moisture retention of compounds according to the present invention as compared to comparative compounds.

The quaternary nitrogen-containing vitamin E or polyethoxylated vitamin E according to the present invention may be represented by the following formula (I):

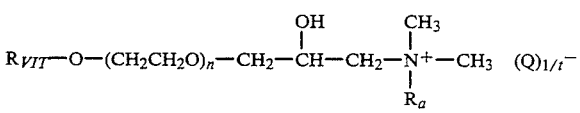

wherein $R_a$ is an alkyl group having up to 12 carbon atoms, or a hydroxyalkyl group having up to 12 carbon atoms and wherein $Q_{1/t}{}^-$ is the anion of a strong inorganic acid of valence t and wherein, $R_{VIT}$—O—, and n have the same meanings as defined above.

Vitamin E radical represented by $R_{VIT}$—O— may have the following structure:

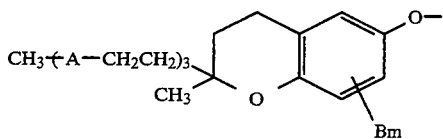

wherein, A is

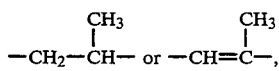

B is —$CH_3$ located at the 5-, 7- or 8- position of tocopherol, and m is an integer from 1 to 3, inclusive.

Vitamin E which is employed for the preparation of the quaternary nitrogen-containing vitamin E derivatives may be synthetic or natural dl-vitamin E or esters thereof. Vitamin E esters may include the acetate, palmitate, succinate and linolate of vitamin E.

When the numerical number n is 0, the product (I) of the present invention is a quaternary nitrogen-containing vitamin E.

Whereas, the numerical number n which indicates the moles of ethylene oxide is an integer from 1 to 30, the product (I) is a quaternary nitrogen-containing polyethoxylated vitamin E. Polyethoxylated vitamin E is an etherified vitamin E and disclosed in U.S. Ser. No. 07/857,652, which is commonly assigned, and may be prepared by subjecting vitamin E to addition reaction with ethylene oxide in the presence of catalyst. The detailed process for preparing polyethoxylated vitamin E is described in the above U.S. Ser. No. 07/857,652, contents of which are incorporated herein as a reference. The moles of ethylene oxide in the polyethoxylated vitamin E molecule, i.e., n may vary in a wide range, and particularly varies between 1 and 30. The polyethoxylated vitamin E retains vitamin E's properties such as anti-oxidation and cell protecting activities as well as shows good compatibility with other active ingredients in cosmetics or drugs when used in cosmetics or drugs.

According to the present invention, the quaternary nitrogen-containing vitamin E derivatives may be prepared by reacting vitamin E or its esters, or polyethoxylated vitamin E with a quaternizing agents which are quaternary ammonium salts to effect substitution of vitamin E or polyethoxylated vitamin E chain. Typical quaternary ammonium salts which can be utilized include quaternary nitrogen-containing halohydrins and epoxides. The quaternary nitrogen-containing halohydrins and epoxides may have the following formula (II-A) and (II-B), respectively.

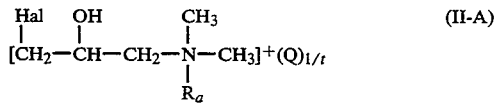

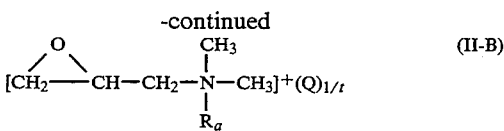

wherein,

Hal is a halogen atom selected from fluorine, chlorine and bromine, $R_a$ is an alkyl group having up to 12 carbon atoms, a hydroxyalkyl group having up to 12 carbon atoms or an alkylene group having up to 12 carbon atoms, Q is a strong inorganic acid, and t is the valency of the Q.

The quaternary nitrogen-containing halohydrins and epoxides may be prepared by known methods, for example the method described in U.S. Pat. No. 2,995,513. Thus, a tertiary amine is reacted with a epichlorohydrin in the presence of a strong inorganic acid and the resulting product is treated with an alkali to give a quaternary halohydrin. Thus obtained quaternary halohydrin is reacted with a strong base such as sodium hydroxide or potassium hydroxide in aqueous solvent to give a quaternary epoxide. The suitable tertiary amine salts which may be employed include, for example, trimethylamine hydrochloride, dimethylcarprylamine hydrochloride and dimethyllaurylamine hydrochloride.

The quaternization reaction of vitamin E or polyethoxylated vitamin E with quaternary halohydrin or epoxide may be effected at temperatures of from about 5° C. to about 80° C., preferably from about 40° C. to about 65° C., for a time required to accomplish the reaction varying from about 0.5 to about 14 hours, particularly from about 3 to about 8 hours. Alkaline catalyst, such as sodium hydroxide, potassium hydroxide, lithium hydroxide, tetramethyl ammonium hydroxide, tetraethyl ammonium hydroxide, and the like, may be employed to accelerate the reaction. The amount of catalyst utilized will depend upon whether the quaternizing agent employed is a holohydrin or epoxide. Where a quaternary halohydrin is employed, an amount of catalyst of from abount 0.1 to 5 moles per mole of qaternary halohydrin is satisfactory, while when the quaternary epoxide is employed, suitable amounts are from about 0.1 to about 3 moles per mole of quaternary epoxide. The proportion of quaternary ammonium salt to vitamin E or polyethoxylated vitamin E may be in the range of from about 0.1 to about 10 moles of quaternary ammonium salt per vitamin E or polyethoxylated vitamin E, preferably from about 1 to about 5 moles per vitamin E or polyethoxylated vitamin E.

The cationic moiety of the quaternary nitrogen-containing vitamin E or polyethoxylated vitamin E is introduced by the quaternary ammonium salts employed for the quaternization. For example, where 3-chloro-2-hydroxypropyltrimethyl ammonium chloride is employed as a quaternary ammonium salt, the anion (Q)$^-$ is a chloride ion.

The quaternary nitrogen-containing vitamin Es or polyethoxylated vitamin Es exhibit an improved substantivity to hair or skin and an improved dispersiblity in water while retaining the physiological activities of the vitamin E or polyethoxylated vitamin E species themselves.

The compounds of this invention may be formulated into the form of emulsion, solution or aerosol by conventional techniques employed in the art. It may be incorporated into, particularly hair-care products such as shampoo, hair rinse, hair-treatment cream, hair lotion or hair tonic; basic skin treatment products such as face cream or lotion; and make-up cosmetics such as foundation or compact powder. It eliminates efficiently the static flyaway of hair and gives a conditioning effect to hair when applied to hair. Moreover, it makes the skin moist, soften and elastic when applied to skin, due to its good sorption onto skin as well as its excellent moisture retention effect.

The amount of quaternary nitrogen-containing vitamin E or polyethoxylated vitamin E to be added to cosmetics may vary depending on the purpose of addition and kind and amount of other active constituents in cosmetics, but generally ranges from about 0.1 to about 50% by weight.

The present invention being generally described, a more complete understanding can be attained by reference to the Examples which are provided herein for purposes of illustration only, and are not intended to limit the invention in any way.

Experimental Example 1

Moisture retention ability

The moisture retention ability of quaternary nitrogen-containing vitamin E (Example 1) or polyethoxylated vitamin E (Example 4) were compared with those of glycerin and sodium pyrrolidone carboxylate(PCA-Na), which are most commonly used as a humectant, and polyoxyethylene(20) sorbitan monostearate.

Solutions of test compounds and distilled water were applied to the skin of healthy volunteers. 30 min or 1 hour later, the hydrations were determined using Corneometer CM 820PC(Schwazhaupt, Germany) and the results are shown in FIG. 1.

As shown in FIG. 1, the quaternary nitrogen-containing vitamin E and polyethoxylated vitamin E species show a potent moisture retention ability and are very soluble in water, and thus may be effectively used as a humectant in cosmetics.

Experimental Example 2

Surface activity

In order to examine the surface activity of the compounds of the present invention, the quaternary nitrogen-containing vitamin E(Example 2) or polyethoxylated vitamin E(Example 5) as well as polyoxyethylene (E.O.=15.02) tocopheryl ether and polyethoxylated.(E.O.=24) cholesterol were tested for surface tension, foaming ability and foam stability.

1. Surface tension

The surface tension of 0.1% aqueous solutions of the test compounds were determined with a surface tension balance manufactured by Fisher Scientific using the method of Du Nouy at 25° C. The results are shown in Table 1. (Du Nouy, "Space Equilibria of Organic and Biological Colloids", Chem. Catalogue, New York, 1926 & Science, 69, 251(1929)).

TABLE 1

| Surface tension | |
|---|---|
| Sample | Surface tension (dyne/cm) |
| Polyethoxylated(E.O. = 24) cholesterol | 37.5 |
| Polyoxyethylene(E.O. = 15.02) tocopheryl ether | 49.0 |
| Compound of Example 2 | 54.3 |

TABLE 1-continued

| Surface tension | |
|---|---|
| Sample | Surface tension (dyne/cm) |
| Compound of Example 5 | 58.9 |

As shown in Table 1, the quaternary nitrogen-containing vitamin E and polyethoxylated vitamin E of the present invention show higher surface tensions than that of polyethoxylated(E.O.=24) cholesterol as a reference which is widely used in cosmetics.

2. Foaming ability and foam stability

The foaming ability and foam stability were determined by a dynamic foam test.

Into a 2 l scaled cylinder of 10 cm inner diameter was placed 400 cc of 0.1% aqueous solution of the test compounds and the solution was stirred at 3000 rpm, 25° C. with an agimixer. The volume of the resultant foam layer was denoted as the foaming ability, and the ratio of the volume of the foam layer just after stirring to the same three minutes after stirring was denoted as the foam stability. The results are shown in Table 2.

TABLE 2

| Foaming ability and Foam stability | | |
|---|---|---|
| Sample | Foaming ability (cc) | Foam stability (%) |
| Polyethoxylated(E.O. = 24) cholesterol | 279 | 91.4 |
| Polyoxyethylene(E.O. = 15.02) tocopheryl ether | 220 | 95.5 |
| Compound of Example 2 | 280 | 91.9 |
| Compound of Example 5 | 289 | 93.1 |

As shown in Table 2, the quaternary nitrogen-containing vitamin E and polyethoxylated vitamin E show potent foaming abilities, which are slightly higher than that of polyethoxylated(E.O.=24) cholesterol as a reference.

Experimental Example 3

Dispersing power

The dispersing power, emulsifying power and emulsion stability of quaternary nitrogen-containing vitamin E or polyethoxylated vitamin E species were evaluated by using the lipsticks and the emulsion foundations having the following compositions. The lipsticks were evaluated for the dispersing power and sweating phenomenon, and the emulsion foundations were evaluated for the dispersing power, emulsifying power and emulsion stability.

Pigment dispersion and emulsion conditions were observed with a polarization microscope and naked eyes at 30° C. Sweating was observed after standing the lipstick at 5° C. and 37° C. in twelve-hour shifts, and emulsion stability was observed with naked eyes after storing at 45° C. for 50 days. The results are shown in Table 3.

| | [Lipsticks] | |
|---|---|---|
| Materials | Inventive | Comparative |
| 1. Castor oil | to 100 | 100 part by weight |
| 2. Wood wax | 5.0 | 5.0 |
| 3. Hydrogenated castor oil | 4.0 | 4.0 |
| 4. Cetostearyl alcohol | 3.0 | 3.0 |
| 5. Paraffin | 2.0 | 2.0 |
| 6. Liquid paraffin | 10.0 | 10.0 |
| 7. Liquid lanolin | 11.0 | 11.0 |

| [Lipsticks] | | |
|---|---|---|
| Materials | Inventive | Comparative |
| 8. Sorbitan sesquioleate | — | 1.0 |
| 9. Quaternary nitrogen-containing vitamin E (Example 3) | 1.0 | — |
| 10. Mica titanium | 8.0 | 8.0 |
| 11. Ferric oxide | 0.2 | 0.2 |
| 12. Calcium lake Red No. 202 | 0.3 | 0.3 |
| 13. Antioxidant | 0.1 | 0.1 |
| 14. Perfume | 0.2 | 0.2 |

Materials 1 to 9 were melted by heating to 80° C., into which materials 10 to 12 were dispersed. The dispersion was degassed and materials 13 and 14 were added thereto. The mixture was cooled to 30° C.

| [Facial emulsion foundations] | | |
|---|---|---|
| Materials | Inventive | Comparative |
| 1. Volatile silicone | to 100 | 100 part by weight |
| 2. Liquid paraffin | 10.0 | 10.0 |
| 3. Sorbitan sesquioleate | — | 3.0 |
| 4. Quaternary nitrogen-containing polyoxy-ethylene (15.0) tocopheryl ether | 3.0 | — |
| 5. Microcrystalline wax | 2.0 | 2.0 |
| 6. Bee wax | 3.0 | 3.0 |
| 7. Paraffin | 3.0 | 3.0 |
| 8. Aluminium stearate | 0.3 | 0.3 |
| 9. Preservative | 0.2 | 0.2 |
| 10. Titanium dioxide | 9.5 | 9.5 |
| 11. Talc | 3.1 | 3.1 |
| 12. Ferric oxide | 0.9 | 0.9 |
| 13. Yellow ferric oxide | 1.4 | 1.4 |
| 14. Black ferric oxide | 0.2 | 0.2 |
| 15. Distilled water | 45.0 | 45.0 |
| 16. Glycerin | 3.0 | 3.0 |
| 17. Magnesium sulfate | 0.4 | 0.4 |
| 18. Perfume | 0.3 | 0.3 |

Materials 1 to 9 were melted by heating to 80° C., into which materials 10 to 14 were dispersed. Materials 15 to 17 were added gradually under heating to 80° C. and the mixture was stirred for 30 min. After adding material 18, the mixture was stirred and cooled to 30° C.

TABLE 3

| | Test item | | | |
|---|---|---|---|---|
| Sample | Dispersion | Emulsion | Sweating | Emulsion stability |
| Lipstick | | | | |
| Inventive | Pigments are homogeneously dispersed | — | No | — |
| Comparative | Pigments are not homogeneously dispersed, but coagulated | — | Sweating is occured on the surface | — |
| Foundation | | | | |
| Inventive | Pigments are homogeneously dispersed | Emulsion particles having a diameter of 1-2 μm are formed | — | No precipitation of the pigment |
| Comparative | Pigments are not homogeneously dispersed, rather coagulated | Emulsion particles having a diameter of 1-6 μm | — | Pigments are precipitated and supernatant |

TABLE 3-continued

| | Test item | | | |
|---|---|---|---|---|
| Sample | Dispersion | Emulsion | Sweating | Emulsion stability |
| | | are formed | | is formed |

Experimental Example 4

Safety in the living body: Primary eye irritation test

In order to evaluate the safety of quaternary nitrogen-containing vitamin E derivatives of the present invention in the living body, the primary eye irritation test was carried out using rabbit according to the Draize procedure [J. H. Draize, "Appraisal of the safety of chemicals in food, drug and cosmetics", Association of Food and Drug Officials of the U.S. Topeka 49(1965)].

A test compound selected from quaternary nitrogen-containing vitamin E obtained in Example 1, quaternary nitrogen-containing polyoxyethylene(15) tocopheryl ether obtained in Example 6 and polyoxyethylene(20) sorbitan monostearate was diluted with 10% aqueous glycerin solution to give 10% test samples.

Six healthy albino rabbits weighing 2 to 3 kg were chosen, and 0.1 ml of the test sample was dropped onto one eye of each rabbit, taking the other eye as a control. 24 hours later, the average scores were recorded according to the Draize scoring for ocular lesions. If lesions were present the time was extended.

The results are shown in FIG. 2.

As shown in Table 3 and FIG. 2, the quaternary nitrogen-containing vitamin E derivatives of the present invention show good dispersibility and are weaker irritant than polyoxyethylene sorbitan monostearate. Therefore, cosmetic compositions containing a quaternary nitrogen-containing vitamin E derivative according to the present invention may be advantageously formulated into skin-care cosmetic compositions such as eye creams, hair-care cosmetic compositions such as shampoos or rinses and make-up cosmetic compositions such as foundations or lipsticks.

Example 1

6 g of synthetic dl-α-tocopherol (BASF) was dissolved into 35 ml of isopropyl alcohol and 17 g of 2,3-epoxypropyltrimethyl ammonium chloride (68% aqueous solution) was gradually added thereto. After the mixture was heated to 40° C., about 1.0 ml of 45% sodium hydroxide was gradually added thereto and the resulting mixture was allowed to react at about 60° C. for about 10 hours. After completion of the reaction, the pH was adjusted to 7.0 with 0.03M hydrochloric acid.

The reaction mixture was evaporated with a vacuum rotary evaporator and an excess of isopropyl alcohol was added to give precipitates. The precipitates were filtered and evaporated with a vacuum rotary evaporator. The dried product was dissolved in a small amount of methanol and subjected to gel chromatography on SEPHADEX LH-20 (SIGMA, USA) column using methanol as an eluant to effect a purification. The desired product-containing fractions were dried with vacuum rotary evaporator to give about 6 g of jelly-like desired product.

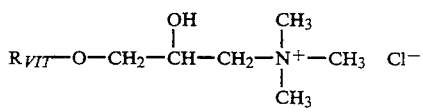

Example 2

6 g of natural dl-α-tocopherol(ROCHE) was dissolved into 40 ml of ispropyl alcohol and 19.0 g of 2,3-epoxypropyldimethyloctyl ammonium chloride (68% aqueous solution) was gradually added thereto under stirring. After the mixture was heated to 60° C., about 0.5 ml of 45% sodium hydroxide was gradually added thereto and the resulting mixture was allowed to react at about 55° C. for about 12 hours. After completion of the reaction, the pH was adjusted to 7.0 with 0.03M hydrochloric acid.

The reaction mixture was evaporated with a vacuum drier and an excess of isopropyl alcohol was added to give precipitates. The precipitates were filtered and evaporated with a vacuum rotary evaporator. The dried product was dissolved in a small amount of methanol and subjected to gel chromatography on SEPHADEX LH-20 (SIGMA, USA) column using methanol as an eluant to effect a purification. The desired product-containing fractions were dried with a vacuum rotary evaporator to give about 8 g of dark brown jelly-like desired product.

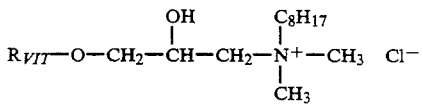

Example 3

10 g of synthetic dl-α-tocopherol(manufactured by BASF) was dissolved in 80 ml of isopropyl alcohol and 30 g of 2,3-epoxypropyldimethyldodecyl ammonium chloride solution(68% aqueous solution) was gradually added thereto under stirring. After the mixture was heated to 60° C., about 1.0 ml of 45% lithium hydroxide was gradually added thereto and the resulting mixture was allowed to react at 65° C. for about 13 hours. After completion of the reaction, the pH was adjusted to 7.0 with 0.05 ml of hydrochloric acid.

The reaction mixture was evaporated with a vacuum drier and an excess of isopropyl alcohol was added to give precipitates. The precipitates were filtered and evaporated with a vacuum rotary evaporator. The dried product was dissolved in a small amount of methanol and subjected to gel chromatography on SEPHADEX LH-20 column(SIGMA, USA) using methanol as an eluant to effect a purification. The desired product-containing fractions were dried with a vacuum rotary evaporator to give about 15 g of dark brown jelly-like desired product.

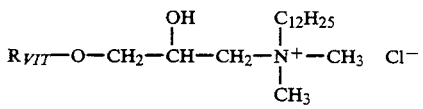

Example 4

(1) In a 1 l double stainless steel autoclave were introduced 144 g of synthetic vitamin E (dl-α-tocopherol) and 0.2 g of KOH (purity 99.9%) and the moisture inside the reactor was removed by heating to 80° C. under vacuum of about 700 mmHg for 30 min. Then, the relative pressure was adjusted to 0.1 kg/cm² by using gaseous nitrogen followed by heating to 150° C.

75 g of ethylene oxide was slowly added thereto under the nitrogen atmosphere and the resulting mixture was reacted under stirring for about 5 hours. The pressure was adjusted to 5 kg/cm² with gaseous nitrogen at the beginning of the reaction. As the reaction proceeded, the pressure became low until it kept constant at which the reaction was ended.

After completion of reaction, the reactor was degassed three times with gaseous nitrogen to remove unreacted ethylene oxide and by-produced 1,4-dioxane. The reaction mixture was cooled to about 20° C., at which it remains in liquid state and small amount of acetic acid was added to neutralize the alkaline catalyst. The reaction mixture was washed with benzene to remove unreacted tocopherol and purified by SEPHADEX LH-20(SIGMA, USA) column chromatography using chloroform-methanol(1:1) to give 221.92 g of liquid polyethoxylated(moles of ethylene oxide=5) vitamin E (yield:98.3%).

(2) Into a reactor equipped with a fractional funnel and a magnetic stirrer was placed 20 ml of isopropyl alcohol and 20 ml of water, and 15 g of polyethoxylated(moles of ethylene oxide=5) tocopherol was added thereto. Then, 0.2 ml of 10% sodium hydroxide solution was added under stirring. After the mixture was heated to about 60° C. and 8.0 g of 70% aqueous 2,3-epoxypropyltrimethyl ammonium chloride solution was gradually added. The mixture was allowed to react at 50° to 55° C. for about 8 hours and neutralized with 0.18 ml of acetic acid. After allowing to stand for 30 min, an excess of isopropyl alcohol was added to give precipitates. The precipitates were filtered and evaporated with a vacuum drier at 45° to 47° C. for about 8 hours to give about 17.8 g of the dark brown jelly-like desired product.

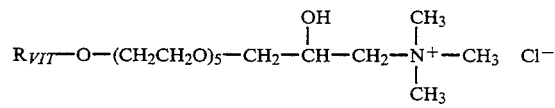

Example 5

25 g of polyethoxylated (moles of ethylene oxide=8) tocopherol prepared in accordance with the procedure in Example 4(1) was dissolved in 30 ml of isopropyl alcohol and 0.2 ml of 10% NaOH was added thereto under stirring. The mixture was heated to 30° C. and 14.5 g of 70% aqueous 2,3-epoxypropyltrimethyl ammonium chloride solution was added dropwise.

The reaction mixture was allowed to react at 55° to 60° C. for 8 hours and neutralized with 0.2 ml of acetic acid. Then, the mixture was again allowed to react for 30 min and an excess of isopropyl alcohol was added to give precipitates. The precipitates were filtered and dried with a vacuum drier at 50° to 55° C. for about 8 hours to obtain about 32 g of the dark brown jelly-like desired product.

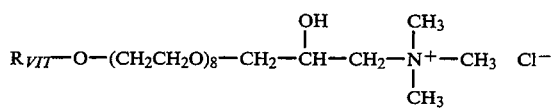

Example 6

Into a reactor equipped with a fractional funnel and a magnetic stirrer were placed 10 g of polyethoxylated(-moles of ethylene oxide=15.0) tocopherol which was prepared in accordance with the procedure in Example 4(1) and dissolved in 80 ml of 50% aqueous isopropyl alcohol solution previously heated to 45° C., 5.0 g of 70% aqueous 2,3-epoxypropyltrimethyl ammonium chloride solution and 0.1 ml of 20% NaOH under stirring. The mixture was allowed to react at 60° C. for 8 hours under stirring and, after completion of the reaction, the pH was adjusted to from 6.8 to 7.0 with acetic acid.

The reaction mixture was concentrated under the reduced pressure and 1 l of isopropyl alcohol was added to give precipitates. The precipitates were filtered off and the filtrate was dried under vacuum to obtain yellow solids. The solids were dissolved in water and subjected to chromatography on SEPHADEX G-15(SIGMA, USA) column using water as an eluant to effect a purification. The fractions containing the desired product were combined and evaporated under vacuum to obtain about 11.2 g of the desired product.

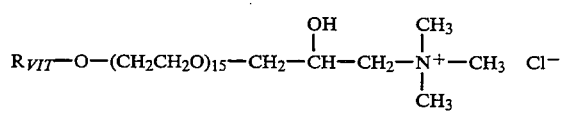

While the invention has been described in its preferred forms by way of Examples, it should be understood that the description is for illustrative purpose only, and the changes and modifications may be made by those skilled in the art without departing from the purpose and spirit of the following claims.

What is claimed is:

1. A quaternary nitrogen-containing vitamin E derivative represented by formula (I):

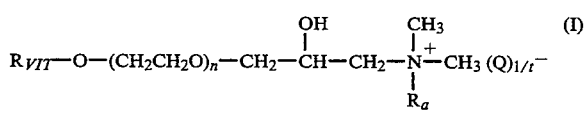

wherein:

$R_{VIT}$—O— is a vitamin E radical represented by the formula:

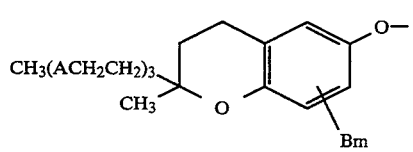

wherein:

A is

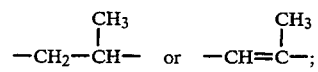

B is —$CH_3$ located at the 5-, 7- or 8- position of tocopherol; and m is an integer from 1 to 3, inclusive, $R_a$ is an alkyl group having up to 12 carbon atoms, or a hydroxyalkyl group having up to 12 carbon atoms;

n is an integer from 0 to 30, inclusive, $O^-_{1/t}$ is the anion of a strong inorganic acid of valence t.

2. The quaternary nitrogen-containing vitamin E derivative according to claim 1 wherein:

$R_{VIT}$—O— is a vitamin E radical represented by the formula:

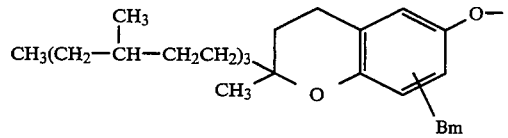

wherein:

B is —$CH_3$ located at the 5-, 7- or 8- position of tocopherol; and m is an integer from 1 to 3, inclusive;

$R_a$ is an alkyl group having up to 12 carbon atoms, or a hydroxyalkyl group having up to 12 carbon atoms; and n is a cypher.

3. The quaternary nitrogen-containing vitamin E derivative according to claim 1 wherein:

$R_{VIT}$—O— is a vitamin E radical represented by the formula:

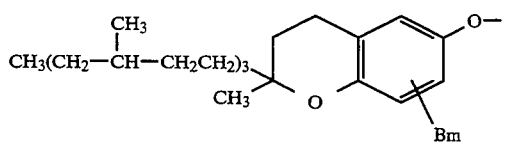

wherein:

B is —$CH_3$ located at the 5-, 7- or 8- position of tocopherol; and m is an integer from 1 to 3, inclusive;

$R_a$ is an alkyl group having up to 12 carbon atoms, or a hydroxyalkyl group having up to 12 carbon atoms; and n is an integer from 1 to 30, inclusive.

4. A skin care composition comprising an effective amount of the quaternary nitrogen-containing vitamin E derivative of claim 1 to moisten, soften and elasticate the skin when applied to skin.

5. A hair care composition comprising an effective amount of the quaternary nitrogen-containing vitamin E derivative of claim 1 to eliminate flyaway of the hair, and give a conditioning effect to hair when applied to hair.

6. A make-up cosmetic composition comprising an effective amount of the quaternary nitrogen-containing vitamin E derivative of claim 1.

7. A cosmetic composition according to claim 6, comprising about 0.1 to about 50% by weight of the quaternary nitrogen-containing vitamin E derivative.

8. A skin care composition according to claim 4, which is an eye cream.

9. A make-up composition according to claim 6, which is a lipstick or foundation.

* * * * *